US012350040B2

(12) United States Patent
Huellen et al.

(10) Patent No.: US 12,350,040 B2
(45) Date of Patent: Jul. 8, 2025

(54) GLUCOSE TEST ARRANGEMENT AND METHOD

(71) Applicant: Roche Diabetes Care, Inc., Indianapolis, IN (US)

(72) Inventors: Volker Huellen, Mannheim (DE); Ingrid Keth, Worms (DE); Beate Koschorreck, Schriesheim (DE); Miguel Setiabudi, Hirschberg (DE); Max Berg, Mannheim (DE); Daniel Kammerer, Mannheim (DE); Ulisse Hohenadel, Weinheim (DE); Daniel Sieffert, Mannheim (DE); Rudolf Pachl, Ellerstadt (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 139 days.

(21) Appl. No.: 16/784,319

(22) Filed: Feb. 7, 2020

(65) Prior Publication Data
US 2020/0275868 A1 Sep. 3, 2020

Related U.S. Application Data

(63) Continuation of application No. PCT/EP2018/070782, filed on Jul. 31, 2018.

(30) Foreign Application Priority Data

Aug. 2, 2017 (EP) .................................... 17184572

(51) Int. Cl.
*A61B 5/145* (2006.01)
*A61B 5/1455* (2006.01)
(Continued)

(52) U.S. Cl.
CPC ........ *A61B 5/14532* (2013.01); *A61B 5/1455* (2013.01); *A61B 5/150022* (2013.01);
(Continued)

(58) Field of Classification Search
CPC .............. A61B 5/14532; A61B 5/1455; A61B 5/150022; A61B 5/150358; A61B 5/157; G01N 33/523
See application file for complete search history.

(56) References Cited

U.S. PATENT DOCUMENTS 8,287,467 B2 * 10/2012 List ...................... A61B 5/1519
600/583
2007/0100365 A1 * 5/2007 Deck ................ A61B 5/150412
606/181
(Continued)

FOREIGN PATENT DOCUMENTS

EP 0503379 A2 9/1992
EP 1424040 A1 6/2004
(Continued)

OTHER PUBLICATIONS

PCT/EP2018/070782; International Search Report and Written Opinion; Sep. 26, 2018.

*Primary Examiner* — Christian Jang
(74) *Attorney, Agent, or Firm* — Woodard, Emhardt, Henry, Reeves & Wagner, LLP

(57) ABSTRACT

A glucose test arrangement is provided for use in a handheld meter. The arrangement comprises a disposable test pad responsive to glucose in a body fluid, and a supporting member adapted to support the test pad at an application site for applying body fluid from a user's skin onto a receiving area of the test pad. The receiving area faces away from the supporting member. One or more spacer elements are arranged on the supporting member adjacent to the test pad,
(Continued)

wherein the one or more spacer elements have a skin-contacting end section which protrudes above the receiving area.

18 Claims, 2 Drawing Sheets

(51) Int. Cl.
    *A61B 5/15*         (2006.01)
    *A61B 5/157*       (2006.01)
    *G01N 21/77*       (2006.01)
    *G01N 21/78*       (2006.01)
    *G01N 33/52*       (2006.01)

(52) U.S. Cl.
    CPC ........ *A61B 5/150358* (2013.01); *A61B 5/157* (2013.01); *G01N 21/78* (2013.01); *G01N 33/523* (2013.01); *G01N 2021/7759* (2013.01); *G01N 2021/7796* (2013.01)

(56) References Cited

U.S. PATENT DOCUMENTS

| | | |
|---|---|---|
| 2008/0049227 A1 | 2/2008 | Sacherer |
| 2008/0103415 A1* | 5/2008 | Roe .................. A61B 5/150358 |
| | | 600/583 |
| 2011/0046453 A1 | 2/2011 | Keil |
| 2011/0263957 A1* | 10/2011 | Thoes ................ A61B 5/14532 |
| | | 600/365 |
| 2014/0186213 A1 | 7/2014 | Dreibholz et al. |

FOREIGN PATENT DOCUMENTS

| | | |
|---|---|---|
| EP | 1535572 A1 | 6/2005 |
| EP | 1878379 A1 | 1/2008 |
| WO | 2003015627 A2 | 2/2003 |
| WO | 2008128688 A1 | 10/2008 |

\* cited by examiner

GLUCOSE TEST ARRANGEMENT AND METHOD

CLAIM OF PRIORITY

The present application is based on and claims priority to PCT/EP2018/070782, filed Jul. 31, 2018, which claims the priority filing benefit of European Application No. 17184572.0, filed Aug. 2, 2017, each of which are hereby incorporated herein by reference in their respective entireties.

TECHNICAL FIELD OF THE INVENTION

The present application relates to a handheld device for measurement of an analyte, particularly to a glucose test arrangement for use in a handheld meter, and more particularly to a disposable test pad for a glucose test in a body fluid, and to a supporting member adapted to support the test pad at an application site for applying body fluid, particularly as a drop of blood, from a user's skin and in particular from a user's finger onto a receiving area of the test pad, wherein the receiving area faces away from the supporting member, such that the sample fluid is applied from the top and the opposite side is flatly supported. The invention specifically concerns a test tape cassette and is further directed to a handheld meter as a glucose concentration measurement device.

BACKGROUND

In the field of blood glucose testing, it is known to use disposable test elements in a handheld glucose meter for measurements on the spot. The user provides a fresh blood sample by pricking a finger and transferring a drop of blood onto the test element. Specifically, a plurality of test elements can be provided for successive use on a test tape, which is loadable into the meter in the form of a replaceable tape cassette. Thus, the user has no need to take care of the disposal of each single test element. However, the instrument is generally used by patients outside a laboratory environment, and therefore the measurement may be susceptible to unintended mishaps due to user handling. For example, contamination on a user's finger, e.g. from food, may lead to additional glucose content in a drop of blood produced on the finger. Thus, false high glucose values may occur if the user does not wash his finger properly before performing a test. Furthermore, some users may tend to press their finger relatively hard onto a test field or test pad, or a user may rub his finger during measurement across the test pad. In extreme cases of user handling scenarios, significant measurement deviations may occur.

On this basis an object of the invention is to further improve the known test arrangements and devices and methods to ensure improved accuracy of the blood glucose measurement during the data acquisition phase or detection phase of a measurement.

The combination of features stated in the independent claims is proposed to achieve this object. Advantageous embodiments and further developments of the invention are derived from the dependent claims.

SUMMARY

The invention is based on the idea of preventing measurements from being distorted due to user handling errors, by aiding a user with regard to sample application to a test field. Thus, a glucose test arrangement is proposed in which one or more spacer elements are arranged on the supporting member adjacent to the test pad, wherein the one or more spacer elements have a skin-contacting end section, particularly a finger-contacting end section, which protrudes above the receiving area of the test pad. In this way, the user receives a tactile feedback already before the test pad is contacted. The skin or finger is prevented from directly pressing onto the test pad, and/or even from contacting the test pad. Only the drop of blood reaches the receiving area of the test pad. Moreover, the spacer elements diminish the risk that the user wipes off contaminated blood from the finger surface. Instead, mostly non-contaminated blood from parts of the blood drop which are farther away from the skin or finger surface is applied to the test pad.

In order to provide the test pad at the application site, the test pad can be moved relative to the supporting member and relative to the spacer elements thereon.

For a test pad having a large-area to be wetted with body fluid, in one embodiment of the present invention a bottom side of the test pad flatly and/or full-facedly abuts against the supporting member, while the receiving area is arranged on a top side of the test pad opposite to the bottom side of the test pad.

In other embodiments, the spacer elements are arranged adjacent to a boundary of the receiving area such that they are bodily separate from the test pad at the application site and without solid connection to the test pad at the application site.

In yet other embodiments, the spacer elements are selected from the group comprising ridges, bars, pins, spikes, edges, rectangles, triangles, and saw-tooth structures.

In order to account for the specific sample application procedure, the spacer elements may have a beveled, chamfered and/or rounded contour.

To achieve the user-aiding effects, in one embodiment the spacer elements are made of a non-elastic material as a rigid formed part.

According to certain embodiments wherein the test pads are rectangularly contoured, the spacer elements are arranged on opposite sides of the test tape carrying the test pads.

In one embodiment, the spacer elements are adapted to provide a haptic feedback to the user during sample application. In one aspect, the end section of the spacer elements has a linear or pointed contact surface for contacting the user's skin.

In other embodiments, the spacer elements are adapted to essentially prevent direct finger contact with the test pad during sample application. Such an arrangement is useful when, for example, the test pad is at least partly compressible or becomes at least partly compressible after wetting.

For an optimized functional value, in certain embodiments the spacer elements have a height in the range from about 0.5 mm to about 5 mm, for example from about 1 mm to about 3 mm.

For a direct measurement at the application site, the supporting member may comprise a window for optically scanning a bottom side of the test pad opposite to the receiving area. In this connection, the window may also contain an optical element or delimit an opening free from an optical element.

In yet other embodiments useful in connection with a tape cassette, the supporting member may be formed as a tip for guiding a transport tape which carries a plurality of test pads spaced apart from each other.

Alternatively, for use of single disposables, the supporting member may be adapted to position a test strip carrying a test pad.

Another aspect of the invention concerns a tape cassette for glucose tests comprising the test arrangement according to the invention, wherein the supporting member is formed as a deflection tip for a transport tape which carries a plurality of test pads spaced apart from each other, and wherein the spacer elements are arranged on both longitudinal sides of the transport tape. In some embodiments, the spacer elements may comprise injection-molded parts.

The invention also concerns a handheld meter for glucose tests comprising the above described tape cassette or test arrangement and a detection unit operable for detecting measuring values on the test pad, using, for example, optical or photometric measurement techniques.

A still further aspect of the invention concerns a glucose test method for use in a handheld meter, comprising the steps of
- providing a disposable test pad which is responsive to glucose in a body fluid,
- placing and positioning the test pad on a supporting member at an application site for body fluid, where one or more spacer elements are arranged on the supporting member adjacent to the test pad,
- applying body fluid, particularly as a drop of blood, from a user's skin onto a receiving area of the test pad, where the receiving area faces away from the supporting member, and
- contacting the user's skin by means of a skin-contacting end section of the one or more spacer elements which protrudes above the receiving area, thereby preventing direct finger contact with the test pad during sample application for enhanced accuracy of the glucose test.

In this way, similar effects and advantages are achieved as already mentioned above.

BRIEF DESCRIPTION OF THE DRAWINGS

In the following, the invention is further elucidated on the basis of an embodiment example shown schematically in the drawings, where.

DETAILED DESCRIPTION OF EMBODIMENTS OF THE PRESENT INVENTION

Figure 1:
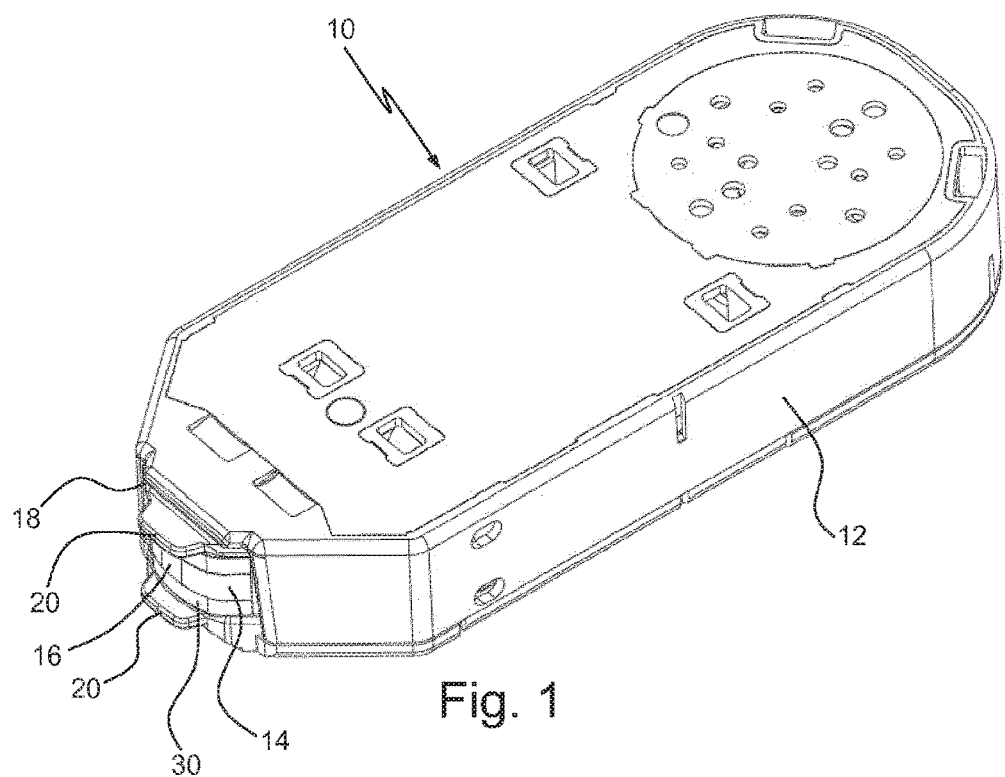
FIG. 1 shows a test tape cassette for glucose tests having a deflection tip and finger-contacting spacer elements projecting from the tip; testing system including.

As depicted in FIG. 1, an exemplary embodiment of a disposable tape cassette 10 for blood glucose tests comprises a housing 12, a spoolable transport tape 14 which carries a plurality of test pads 16 spaced apart from each other and a deflection tip 18 for successive provision of the test pads 16 on the tip 18 for sample application in contact with a user's finger, wherein protruding spacer elements 20 on the tip 18 provide a haptic feedback to the user during sample application and prevent direct skin or finger contact with the test pad. Forwarding of the transport tape 14 is accomplished by two spools as in a conventional audio or video cassette (not shown).

Figure 2:
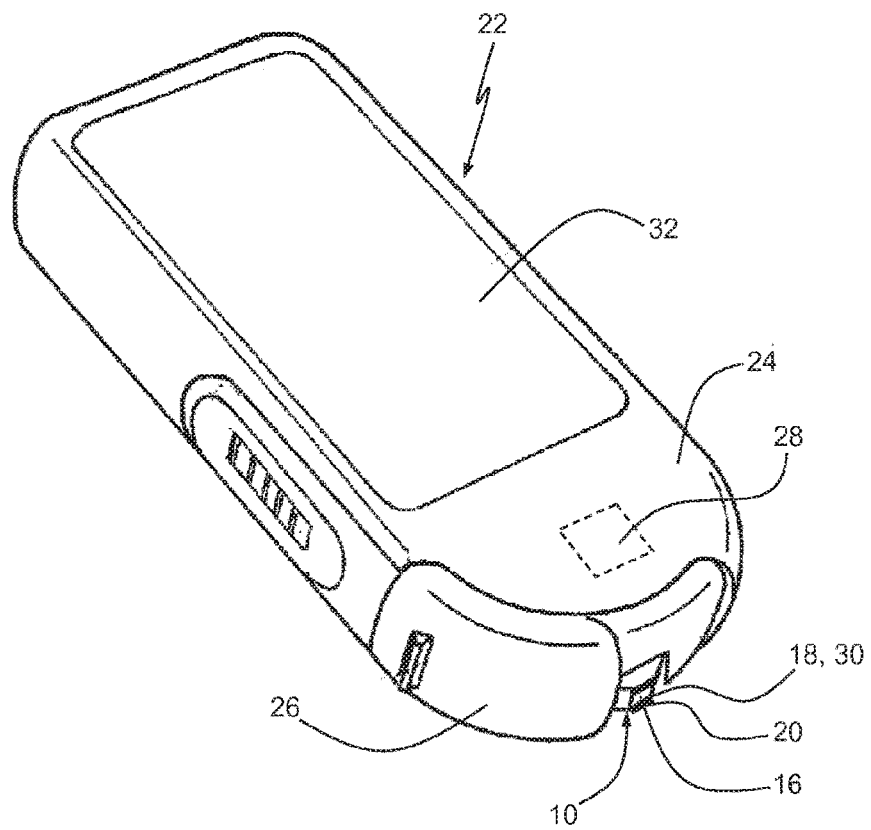
FIG. 2 is a perspective view of a handheld glucose meter configured for using the test tape cassette.

As further shown in FIG. 2, a portable glucose meter 22 is adapted to receive the disposable test tape cassette 10 which can be inserted into a compartment of the meter housing 24. The tip 18 of the inserted tape cassette 10 is accessible upon opening a tip cover 26. Then, the user applies a drop of blood by pricking a finger with a lancing aid and contacting the top side of the test pad 16. During this handling step, the tip 18 serves as a supporting member 30 underneath the test pad 16.

The handheld meter 22 may be provided with a photometric-type measuring unit 28 for determining a glucose concentration from the measured values. For this purpose, the test pads 16 on the transport tape 14 are formed by a layered chemistry field which is responsive to the analyte, such as glucose, by a color change. Then, the measuring unit 28 allows a measurement of the analyte concentration by optical scanning of the rear side of transport tape 14 at the location of a dosed test pad 16, through an optical window in the support member 30 and the transparent transport tape 14. The measuring result and other information can be displayed to the user on a display 32.

Figure 3:
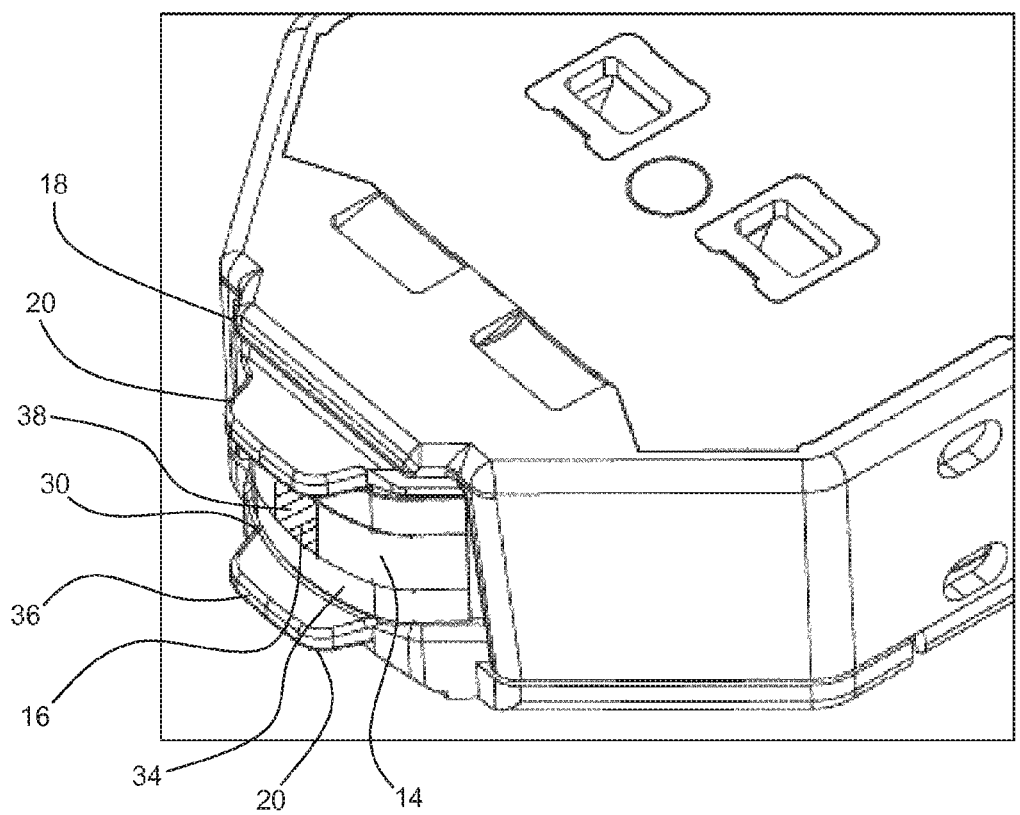
FIG. 3 is an expanded cut-out from FIG. 1.

As apparent from FIG. 3, the spacer elements 20 are arranged laterally to the tape 14 as a rigid unitary structure of the tip 18, made, for example, as injection-molded parts. These are formed as ribs or ridges protruding from the flat or curved supporting surface 34 of the supporting member 30. The linear skin-contacting end section 36 of the spacer elements 20 protrudes above the upper fluid (blood) receiving area 38 of the active test pad 16 on the tip 18. As the test pad 16 may be at least partly compressible or may become at least partly compressible after sample application, the spacer elements 20 should have a sufficient height in the range of about 0.5 mm to about 5.0 mm, such as from about 1 mm to about 3 mm, measured from the surface of the supporting member 30, in order to avoid direct finger pressure. Pressure from a finger after wetting may lead to an unwanted modification of the layered test structure, for example if a covering net or mesh is provided for sample spreading it may become impressed into the chemistry field, thus impairing or impacting an optical measurement.

The spacer elements 20 may be arranged on opposite sides of the test pad 16. As shown, the test pad 16 has a rectangular contour. Thereby, the user receives tactile feedback information before his finger reaches the test pad 16. In this way, excessive exertion of pressure can be avoided. Furthermore, the spacer elements 20 may provide a certain stability for the applying finger, for example by reducing unwanted finger movement during sample application, such as due to tremor.

Figure 4:
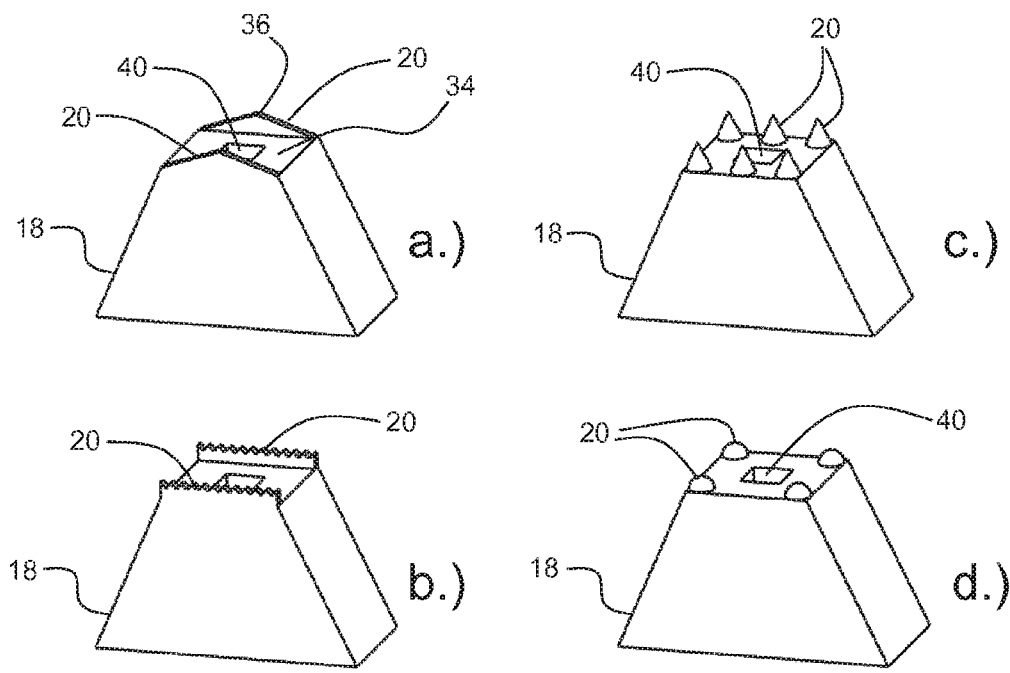
FIG. 4 illustrates various alternative forms of spacer elements on the tip, denoted as a.), b.), c.) and d.).

FIG. 4 schematically shows various alternative embodiments of spacer elements 20 on a cassette tip 18. In FIG. 4a, the spacer elements 20 have a chamfered, triangular shape ending in a pointed contact surface 36. Also apparent is an optical window 40 in the center of the supporting surface 34 for reflectometric measurement. FIG. 4b shows saw-toothed structures of spacer elements 20, whereas FIG. 4c and FIG. 4d illustrate spikes and rounded pins as spacer elements 20.

EXAMPLE

The improvement with the design according to an embodiment of the present invention was demonstrated in a comparative study, the results of which are given in Table 1 below. In the study, tape cassettes 10 with and without spacer elements 20 on the supporting member 30 have been used. In the glucose concentration range below 100 mg/dL, results in a commonly used benchmark interval of +/−10 mg/dL (+/−0.56 mmol/L) from reference values have been approved, whereas in the higher range of 100 mg/dL and above results in a relative interval of +/−10% from reference values have been counted as acceptable. The reference glucose values for the samples were determined using a hexokinase methodology (hexokinase/glucose-6-phosphate-dehyrogenase) and a commercially available Cobas 6000 c501 analyzer system. The obtained results clearly demonstrate the enhanced precision of the analyte measurements employing the spacer elements 20 on the tape cassette tip.

TABLE 1

Comparative study of tape cassette design

|  |  | Cassette without spacer elements (conventional) | Cassette with spacer elements (inventive design) |
|---|---|---|---|
| Glucose concentration <100 mg/dL | Result within +/−10 mg/dL from reference value | 98.7% (154/156) | 99.5% (185/186) |
| Glucose concentration ≥100 mg/dL | Result within +/−10% from reference value | 92.3% (410/444) | 99.3% (411/414) |

What is claimed is:

1. A glucose test method for use in a handheld meter, comprising:
    providing a disposable test pad which is responsive to glucose in a body fluid, the test pad having a top side and an opposite bottom side and a receiving area arranged on the top side,
    positioning the test pad on a supporting member at an application site for body fluid, the supporting member further comprising one or more spacer elements arranged adjacent to the application site, the test pad being movable relative to the supporting member,
    applying a drop of blood from a user's skin onto the receiving area of the test pad, where the receiving area faces away from the supporting member,
    contacting the user's skin by means of a skin-contacting end section of the one or more spacer elements which protrudes above the receiving area, thereby preventing direct finger contact with the test pad during sample application for enhanced accuracy of the glucose test.

2. A glucose test arrangement for use in a handheld meter, comprising:
    a supporting member having an application site and one or more spacer elements arranged adjacent to and on opposed sides of the application site;
    a pair of tape spools;
    a transport tape stored on and extending between the pair of tape spools; and
    a plurality of flat, spaced apart test pads carried by the transport tape, each test pad being responsive to glucose in a body fluid and each having a top side comprising a receiving area and an opposite bottom side, the transport tape being movable relative to the supporting member,
    the supporting member supporting the transport tape and one of the test pads at the application site for application of a drop of blood from a user's skin onto the receiving area,
    the bottom side of the test pad fully and flatly abutting the supporting member and the receiving area facing away from the supporting member
    each of the one or more spacer elements having a skin-contacting end section which protrudes outwardly from the application site in a direction orthogonal to the application site, the skin-contacting end section extending beyond the top side of the test pad, and
    the one or more spacer elements providing a haptic feedback to the user and preventing direct finger contact with the test pad during sample application.

3. The arrangement according to claim 2, wherein the spacer elements are arranged adjacent to a boundary of the receiving area such that they are bodily separate from the test pad at the application site and without solid connection to the test pad at the application site.

4. The arrangement according to claim 2, wherein each skin-contacting end section is selected from the group comprising ridges, bars, pins, spikes, edges, rectangles, triangles, and saw-tooth structures.

5. The arrangement according to claim 2, wherein each skin-contacting end section has a beveled, chamfered and/or rounded contour.

6. The arrangement according to claim 2, wherein the end section of the spacer elements has a linear or pointed contact surface positioned to contact the user's skin.

7. The arrangement according to claim 2, wherein the spacer elements are made of a non-elastic material as a rigid formed part.

8. The arrangement according to claim 2, wherein the spacer elements are provided on the supporting member so as to be arranged on opposite sides of the test pad provided at the application site.

9. The arrangement according to claim 2, wherein the test pad is at least partly compressible or becomes at least partly compressible after sample application.

10. The arrangement according to claim 2, wherein the spacer elements have a height in the range from 0.5 mm to 5 mm.

11. The arrangement according to claim 10, wherein the height is in the range from 1 mm to 3 mm.

12. The arrangement according to claim 2, wherein the supporting member comprises a window in the support surface for optically scanning the bottom side of the test pad opposite to the receiving area.

13. The arrangement according to claim 12, further comprising a photometric detection unit operable for detecting measuring values on the test pad.

14. The arrangement of claim 12, wherein the window contains an optical element or delimits an opening free from an optical element.

15. The arrangement according to claim 12, wherein the supporting member positions a test strip carrying the test pad.

16. The arrangement according to claim 2, wherein the test pad is carried on a transport tape comprising a plurality of further test pads each spaced apart from each other, and wherein the supporting member is formed as a tip guiding the transport tape.

17. The arrangement according to claim 2, wherein the arrangement comprises a tape cassette for glucose tests, wherein the supporting member is formed as a deflection tip for a transport tape which carries the test pad and a plurality of further test pads spaced apart from each other, and wherein the spacer elements are provided on the supporting member and arranged on both sides of the transport tape and comprise injection-molded parts.

18. A tape cassette for glucose tests, the tape cassette comprising:

a housing containing a transport tape carrying a plurality of spaced apart test pads, the transport tape being guided between two spools in the housing,
  wherein between the spools each test pad is successively provided across a tip of the housing, each said test pad comprising a layered chemistry field responsive to glucose contained in an applied fluid sample by a color change,
  the transport tape being transparent at least at the location of each test pad, and each test pad further comprising a receiving area having a planar top surface for application of the fluid sample;
  said tip comprising a planar supporting member having an optical window therein, wherein the glucose-responsive color change in said test pad is observable through the optical window when the fluid sample is applied from a user's skin to one of the test pads positioned over the optical window for optical scanning of a rear side of the transport tape at the location of said test pad, said rear side fully and flatly abutting the supporting member and being on an opposite side of the transport tape from the plurality of test pads,
the supporting member having a pair of spacer elements arranged on opposite sides of the transport tape, wherein said transport tape is guided across the supporting member and between the spacer elements,
said spacer elements comprising a skin-contacting end section which protrudes above the supporting member and extends in a direction orthogonal to the plane of the supporting member and the planar top surface of the receiving area of one of the test pads provided at the application site, and
wherein said spacer elements are configured to provide a haptic feedback to a user and prevent direct contact of a user's finger with the receiving area of the test pad when applying the fluid sample.

\* \* \* \* \*